US00PP24264P2

(12) United States Plant Patent
Mak

(10) Patent No.: US PP24,264 P2
(45) Date of Patent: Feb. 25, 2014

(54) LILY PLANT NAMED 'TINY DANCERS'

(50) Latin Name: *Lilium hybrida*
Varietal Denomination: Tiny Dancers

(75) Inventor: Niels Johannes Cornelis Mak, Wieringerwerf (NL)

(73) Assignee: Mak 't Zand B.V., 't Zand (NL)

( * ) Notice: Subject to any disclaimer, the term of this patent is extended or adjusted under 35 U.S.C. 154(b) by 18 days.

(21) Appl. No.: 13/507,520

(22) Filed: Jul. 5, 2012

(51) Int. Cl.
*A01H 5/00* (2006.01)

(52) U.S. Cl.
USPC ..... Plt./315

(58) Field of Classification Search
USPC ..... Plt./315
See application file for complete search history.

(56) References Cited

PUBLICATIONS

UPOV-ROM PBR LEL 2876, published Dec. 16, 2010, 3 pages.*

* cited by examiner

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of Lily plant named 'Tiny Dancers', characterized by its compact and upright plant habit; vigorous growth habit; densely-foliated habit; freely flowering habit; upright flower buds and flowers; light red to red purple-colored flowers with white-colored centers; and good postproduction longevity.

1 Drawing Sheet

Botanical designation: *Lilium hybrida.*
Cultivar denomination: 'TINY DANCERS'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Tiny Dancers'.

The new Oriental Hybrid Lily plant is a product of a planned breeding program conducted by the Inventor in 't Zand, The Netherlands. The objective of the breeding program is to develop new potted Oriental Hybrid Lily plants with erect flowers, attractive flower coloration and good postproduction longevity.

The new Oriental Hybrid Lily plant originated from a cross-pollination in 2001 of two different unnamed proprietary seedling selections of *Lilium hybrida*, not patented. The new Oriental Hybrid Lily plant was discovered and selected by the Inventor as a single flowering plant from within the resultant progeny of the cross-pollination in a controlled greenhouse environment in 't Zand, The Netherlands in May, 2004.

Asexual reproduction of the new Oriental Hybrid Lily plant by bulb scales in a controlled greenhouse environment in 't Zand, The Netherlands since November, 2004 has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiny Dancers'. These characteristics in combination distinguish 'Tiny Dancers' as a new and distinct Oriental Hybrid Lily plant:

1. Compact and upright plant habit.
2. Vigorous growth habit.
3. Densely-foliated habit.
4. Freely flowering habit.
5. Upright flower buds and flowers.
6. Light red to red purple-colored flowers with white-colored centers.
7. Good postproduction longevity.

Plants of the new Oriental Hybrid Lily differ primarily from plants of the female parent seedling selection in the following characteristics:

1. Plants of the new Oriental Hybrid Lily are more compact than plants of the female parent seedling selection.
2. Flower tepals of plants of the new Oriental Hybrid Lily are broader than flower tepals of plants of the female parent seedling selection.

Plants of the new Oriental Hybrid Lily differ primarily from plants of the male parent seedling selection in flower color as plants of the male parent selection have red-colored flowers.

Plants of the new Oriental Hybrid Lily can be compared to plants of Oriental Hybrid Lily 'Tiny Todd', disclosed in U.S. Plant Pat. No. 16,170. Plants of the new Oriental Hybrid Lily differ from plants of 'Tiny Todd' in the following characteristics:

1. Plants of the new Oriental Hybrid Lily are more compact than plants of 'Tiny Todd'.
2. Plants of the new Oriental Hybrid Lily have thicker flower buds than plants of 'Tiny Todd'.

3. Flowers of plants of the new Oriental Hybrid Lily are darker in color than flowers of plants of 'Tiny Todd'.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant.

The photograph comprises a side perspective view of a typical flowering plant of 'Tiny Dancers'.

DETAILED BOTANICAL DESCRIPTION

The aforementioned photograph and following observations and measurements describe plants that were grown during the spring in 15-cm containers in a glass-covered greenhouse in 't Zand, The Netherlands and under cultural conditions typically used in Oriental Hybrid Lily production. During the production of the plants, day temperatures averaged 15° C., night temperatures averaged 18° C. and light levels averaged 6,000 lux. Measurements and numerical values represent averages for typical flowering plants. Plants were 60 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Tiny Dancers'.

Parentage:

*Female, or seed, parent.*—Unnamed proprietary seedling selection of *Lilium hybrida*, not patented.

*Male, or pollen, parent.*—Unnamed proprietary seedling selection of *Lilium hybrida*, not patented.

Plant description:

*Plant form and growth habit.*—Upright flowering plant; single erect flowering stem with a terminal cluster of flowers; compact and dense plant habit; vigorous growth habit.

*Plant height, soil level to top of flowers.*—About 25 cm.

*Plant diameter, or spread.*—About 19 cm.

*Plant circumference.*—About 60 cm.

*Bulbs.*—Diameter: About 10 cm to 20 cm. Texture: Smooth. Color: Close to 155D.

*Flowering stems.*—Diameter: About 5 mm. Internode length: About 1 cm. Strength: Strong. Texture: Smooth, glabrous. Color: Close to 137A; towards the apex, close to 138A.

*Leaves.*—Arrangement and quantity: Alternate; simple; sessile; about 88 leaves develop per plant. Length, upper leaves: About 8 cm. Width, upper leaves: About 1 cm. Length, lower leaves: About 6.5 cm. Width, lower leaves: About 1 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 137A; venation, close to 137A. Developing and fully expanded leaves, lower surface: Close to 138A; venation, close to 138A.

Flower description:

*Flower shape and aspect.*—Flowers umbellate or funnel-shaped; when fully opened, flowers flatten and tepals recurve towards the apex; flower buds face upright and flowers face upright to slightly outwardly.

*Flowering habit.*—Freely flowering habit, large bulbs will produce seven to ten flowers per flowering stem.

*Fragrance.*—Slightly fragrant.

*Natural flowering season.*—Plants flower in June and July in The Netherlands; plants can be flowered year-round in the greenhouse and forced to bloom about 60 days after planting bulbs.

*Postproduction longevity.*—Good postproduction longevity, flowers last about ten to twelve days on the plant; tepals not persistent; gynoecium persistent.

*Flower buds.*—Length: About 6.5 cm. Diameter: About 3 cm. Circumference: About 8 cm. Shape: Lanceolate. Color: Between 54A and N57D; sutures, between 54A and N57D.

*Flower size.*—Diameter: About 14 cm. Length (height): About 4 cm.

*Perianth.*—Quantity and arrangement: Six tepals per flower arranged in two whorls; tepals imbricate. Tepal length, inner tepals: About 7.5 cm. Tepal width, inner tepals: About 5 cm. Tepal length, outer tepals: About 8 cm. Tepal width, outer tepals: About 3.5 cm. Tepal shape: Lanceolate. Tepal apex: Acute. Tepal margin: Entire. Tepal texture, upper and lower surfaces: Smooth, glabrous. Tepal color: When opening and fully opened, upper surface: Between 54A and N57D; centers and towards the base, close to 158D; spots, close to 184A; color becoming closer to 180C with development. When opening and fully opened, lower surface: Between 54A and N57D.

*Pedicels.*—Angle: About 45° to 70° from vertical. Strength: Strong. Length: About 4.5 cm. Diameter: About 4 mm. Texture: Smooth, glabrous. Color: Close to 138A.

*Reproductive organs.*—Stamens: Quantity per flower: Six. Filament length: About 5.5 cm. Filament color: Between 155D and 38D. Anther length: About 1 cm. Anther color: Close to 181A. Pollen color: Close to 179A. Pistils: Quantity per flower: One. Style length: About 4.5 cm. Style color: Between 155D and 39B. Stigma diameter: About 5 mm. Stigma shape: Lobed. Stigma color: Close to 167D.

*Fruits.*—Length: About 1.2 cm. Diameter: About 4 mm. Color: Close to 146D.

*Seeds.*—No viable seeds have been observed on plants of the new Oriental Hybrid Lily plant.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Tiny Dancers' as illustrated and described.

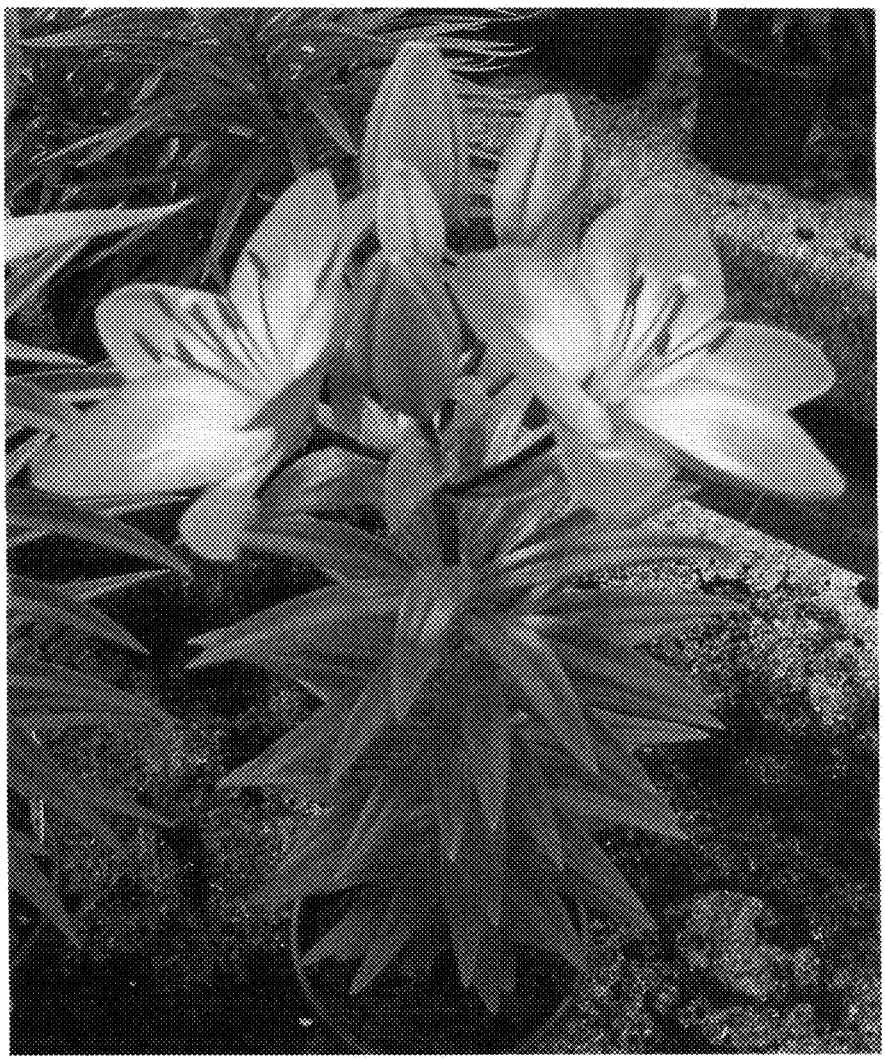

* * * * *